United States Patent [19]

Haas

[11] 4,019,052
[45] Apr. 19, 1977

[54] ELECTROPHOTOGRAPHIC X-RAY DEVICE
[75] Inventor: David J. Haas, Stanford, Conn.
[73] Assignee: U.S. Philips Corporation, New York, N.Y.
[22] Filed: Oct. 30, 1975
[21] Appl. No.: 627,110
[52] U.S. Cl. .......................... 250/274; 250/315 A
[51] Int. Cl.² .................. G01N 23/20; G21K 1/00
[58] Field of Search .......... 250/272, 274, 275, 315, 250/315 A, 273

[56] References Cited
UNITED STATES PATENTS 2,666,144   1/1954   Schaffert et al. .............. 250/315 A
3,792,269   2/1974   Grienauer ........................ 250/275

OTHER PUBLICATIONS

Haas et al., "A New Concept in Automated X-Ray Powder Diffractometry," *Norelco Rep.*, (USA), vol. 18, No. 2, Dec. 1972, p. 12.

*Primary Examiner*—Alfred E. Smith
*Assistant Examiner*—T. N. Grigsby
*Attorney, Agent, or Firm*—Frank R. Trifari; Leon Nigohosian

[57] ABSTRACT

An electrophotographic diffractometer apparatus, comprising a photoconductive storage member, means for uniformly charging said storage member, means for holding a diffraction specimen, means for directing a collimated beam of electromagnetic radiation to said specimen, whereby diffracted rays of said beam are directed to said charge storage member and produce discharged local areas thereon in accordance with the diffraction characteristics of said specimen, and scanning means for electrically measuring the charge pattern at said storage member.

13 Claims, 4 Drawing Figures

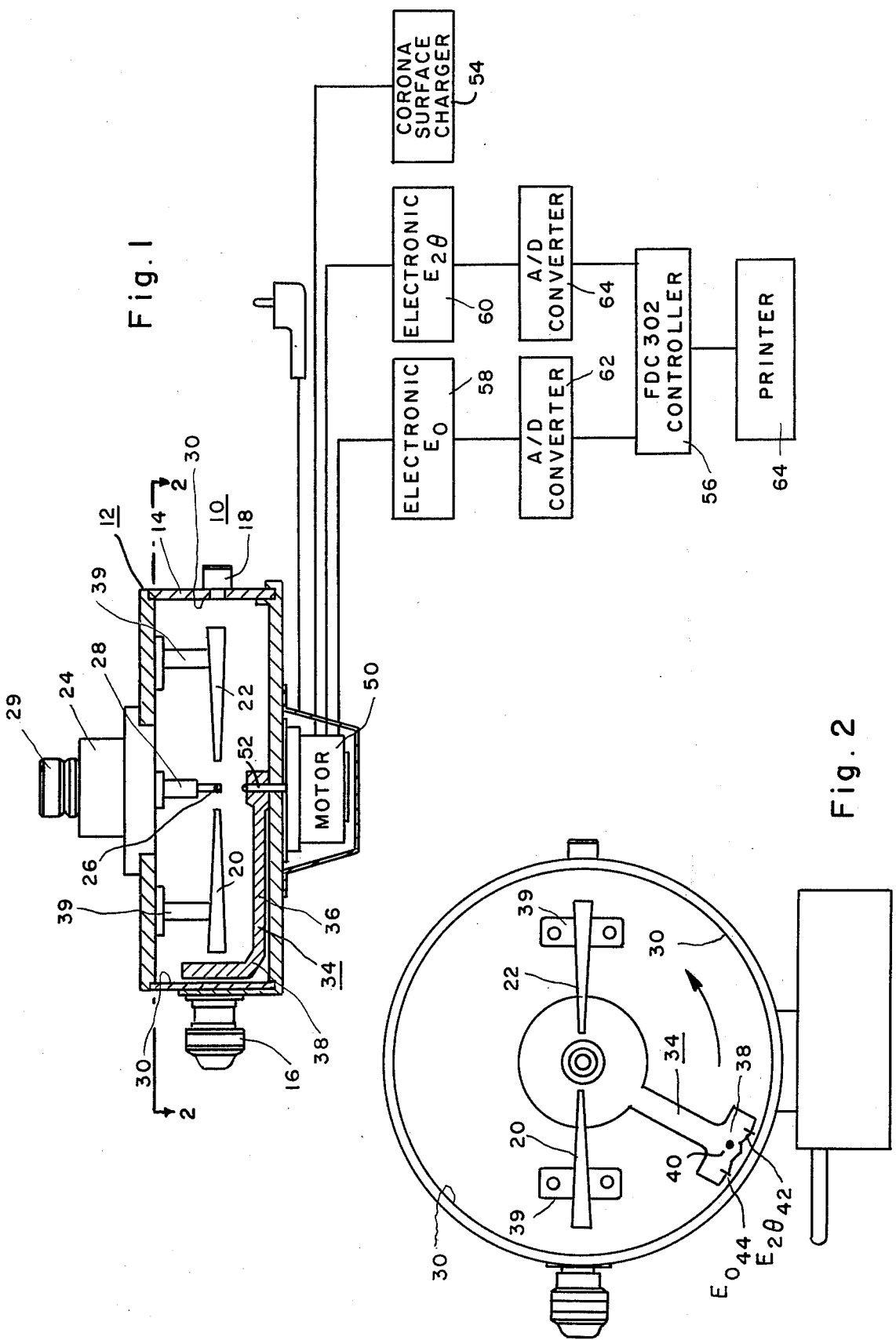

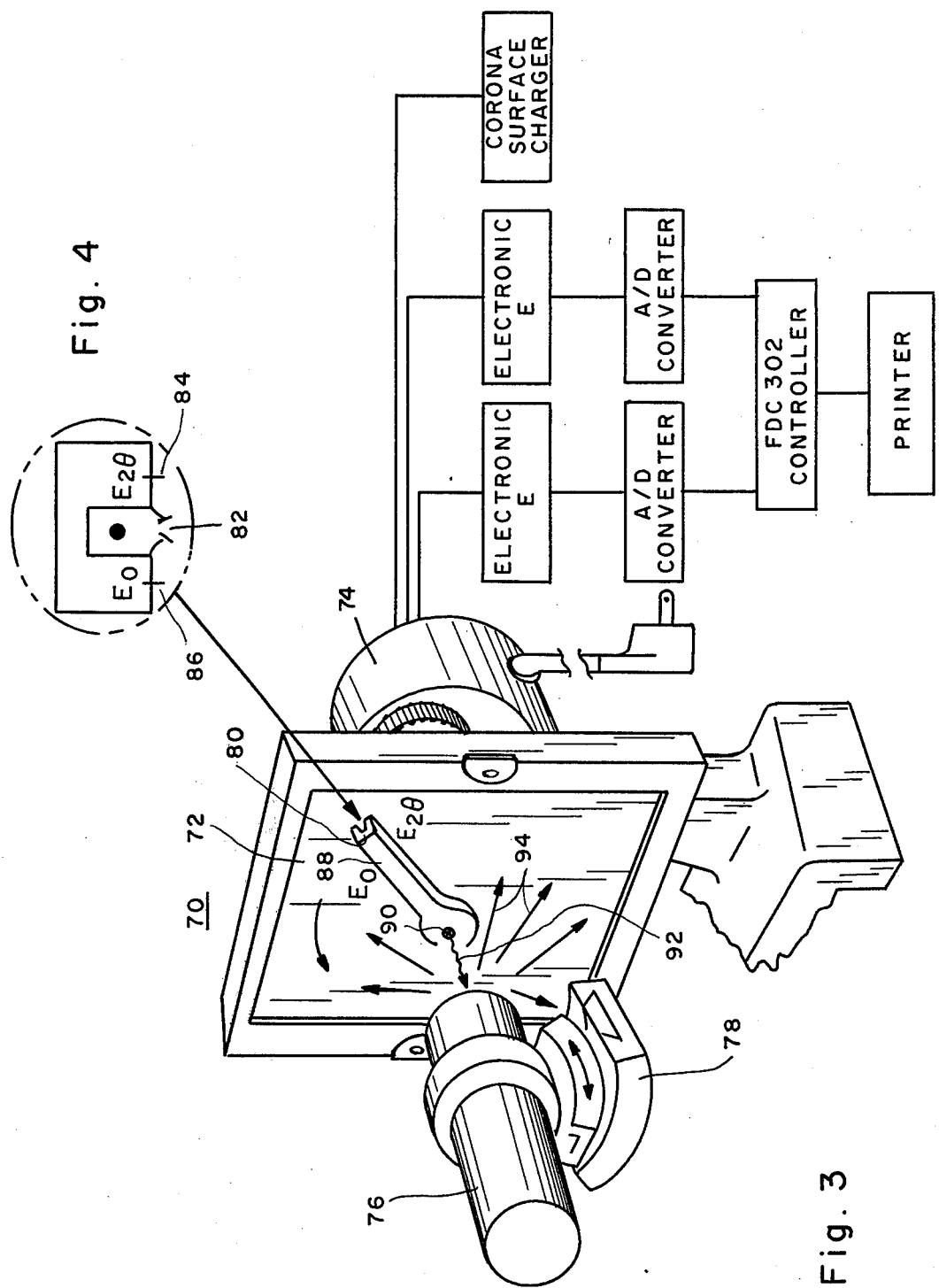

ELECTROPHOTOGRAPHIC X-RAY DEVICE

The present invention relates to a diffractometer apparatus, particularly to an electrophotographic x-ray diffractometer.

The standard x-ray powder camera well-known to the art utilizes a two-dimensional continuous film on which there is recorded the entire two-dimensional powder diffraction pattern. Such a diffractometer suffers from a number of disadvantages, including the fact that the film requires considerable exposure and must be developed for visual read-out. Another prior art device is the x-ray powder diffractometer that utilizes a dynamic detector (scintillation, proportional, or geiger measuring devices) and that records the diffraction pattern by a sequential scan technique. Such a device requires a relatively high intensity x-ray source and requires that the power source be highly regulated in order to make the diffracted intensity time-independent. Such a device is, also, rather complicated and considerably more costly than photographic methods.

The present application seeks to provide advantages over these prior art devices and to overcome some of the shortcomings of these devices.

BRIEF DESCRIPTION OF THE INVENTION

The diffractometer apparatus of the present invention comprises a photoconductive storage member, means for uniformly charging the storage member, means for holding a diffraction specimen which can be a powder, means for directing a collimated x-ray beam to the specimen from various orientations with respect to the specimen so that the diffracted x-rays from the beam are directed to the charge storage member or layer and produce thereon discharged local areas in accordance with the diffraction pattern characteristics of the specimen.

Further included is means for scanning the storage member to electrically measure the charge pattern thereon, as a result of which the diffraction pattern can be read-out.

According to a first preferred embodiment, the photoconductive storage member extends along the entire side wall of the diffractometer device and the specimen is rotated to permit the x-ray beam's striking the specimen from various orientations.

According to another embodiment, the photoconductive member is substantially flat and the primary x-ray beam passes through the photoconductive storage member, striking the specimen which can be rotated if desired, and back-reflecting the beam toward the photoconductive storage member to produce a charge pattern representative of the characteristics of the specimen.

According to a preferred embodiment the storage member comprises a layer of selenium disposed on a conductive substrate with the selenium directly accessible to the diffracted x-ray beam portions. Also, the charging means and the scanning means are preferably disposed on a single rotating member that rotates about the sample or specimen. An apparatus that can be used for the scanning means is a non-contact electrostatic voltmeter that revolves about the specimen holder to provide an analog signal read-out of the diffraction pattern. The charging means can be a corona charger that is supported on the same rotating arm as the electrostatic voltmeter, which corona charger can be turned on and off at will to recharge the plate when required or desirable.

The present apparatus further includes means for converting the analog detector signal to digital data for processing a system control by a digital controller and, furthermore, preferably includes automatic feedback and display facilities.

DESCRIPTION OF THE DRAWINGS

FIG. 1 is a sectional side elevation view of the present electrophotographic x-ray device according to a preferred embodiment.

FIG. 2 is a sectional top view of the device of FIG. 1.

FIG. 3 is a perspective view of a further embodiment utilizing a substantially flat photoconductive storage member.

FIG. 4 is an end elevation view of a non-contact scanning means of a type employable with the present invention.

DESCRIPTION OF THE PREFERRED EMBODIMENT

The electrophotographic diffractometer apparatus 10 (FIG. 1) of the present invention comprises a housing 12 that can be generally of cylindrical shape and that contains a side wall portion 14, within which housing 12 there is located an inlet port 16 and an outlet port 18 and a primary collimator 20 and a secondary collimator 22 disposed between and aligned with the openings of the inlet and outlet ports 16 and 18. At the top of the apparatus 10 there is disposed a holder structure 24 by means of which a specimen sample 26 can be held in position in the path of an x-ray beam passing through the collimator 20, 22, which support comprises a rotatable element 28 on which the sample is disposed and by means of which the same can be rotated, the sample usually being a powder sample of some material. A belt drive (not shown) or other suitable arrangement can be employed to drive the rotatable element 28, the drive mechanism engaging, for example, the rotatable shaft 29.

The apparatus 10 further comprises a storage layer 30 of photoconductive material, e.g., selenium or other suitable material, disposed at the inside surface of the side wall 14 and a rotatable arm member 34 located within the housing and rotatable about the specimen 26. Where it is desired, the relative positions of the holder structure 24 and arm member 34 can be reversed, with the latter being above the former. The rotatable member 34 comprises a first arm portion 36 and a second portion that constitutes the sensing head 38 thereof, which sensing head sweeps along proximate to the photoconductive layer 30. To permit the sensing head 38 to move along a path adjacent the photoconductive layer 30, the collimators 20 and 22 are preferably spaced from the wall 14 and layer 30 and can, as shown, be held by support elements 39 attached to the housing 12. The sensing head 38 (FIG. 2) preferably includes the elements for providing on the photoconductive layer 30 a substantially uniform charge and the element for measuring the charge on the photoconductive layer 30. The charging means can be a rotating corona discharge device 40 such as, for example, a fine wire that is charged to several thousand volts, while the measuring means which scans the charge photoconductive layer can be a non-contact electrostatic voltmeter that comprises two surface charge sensors or electron probes 42, 44 that are located on the symmetrical plane of the rotating member 34, with the corona discharge device 40 located therebetween. The leading electrometer probe 42 measures the residual surface charge $E_{2\theta}$ while the following electrometer probe 44 measures the maximum surface charge $E_0$, these values being fed into an electronic measurement system according to a preferred embodiment, which provides the $E_{2\theta}$ and relative intensity data of the analysis.

In the operation of the invention, the specimen is located in the housing and the rotating member 34 is set in motion, x-rays being admitted and exiting via the collimators 20 and 22, respectively. The corona charge device 40 is activated so as to charge the storage layer 30 substantially uniformly, it being preferably operated so as to maximize the rate at which the storage layer 30 is charged, and especially preferred that the storage layer be fully charged with a single rotation of the charge device 40.

Because the x-rays are diffracted by the specimen in accordance with the particular characteristics of the latter, the diffracted x-rays selectively discharge the storage layer 30 and thus produce a corresponding residual charge pattern which can be read by one of the charge sensors or electron probes, e.g., by the leading electrometer probe 42. The greatest degree of discharge of the storage layer occurs at those portions corresponding to the diffraction peaks, with lesser discharge occuring at portions corresponding to weaker diffraction lines (i.e., at less intense diffraction lines). The charge pattern $E_{2\theta}$ is intermittently read-out by the probe 42 and when the information embodied in the charge pattern is used, the charge is refreshed by one or more succeeding sweeps of the charge device 40. The other (i.e., the following) electrometer probe 44 can measure both the various charge levels of the residual charge pattern produced by discharge (i.e., the extent of discharge) and the levels of the charges produced on the storage layer 30 by the charge device 40 (i.e., the extent of re-charging) and, thus provides a read-out of the residual charge pattern produced by the diffraction lines. By so doing, the scanning probe 44 can be used to determine when the storage layer 30 has been discharged to a level at or approaching zero volts (which level would occur first at the portions of the storage layer corresponding to the diffraction peaks) and the exposure of the charged storage layer to the diffracted x-rays, i.e., the storage layer discharge operation, can be continued until that time. The weaker diffraction lines are thereby permitted to be brought out (i.e., "written into" the storage layer) to a greater extent and the relative intensities of the diffraction lines can be maintained. Were the discharge of the storage layer to be continued beyond such time that the parts thereof corresponding to the diffraction peaks were discharged to zero volts, the discharge of the other parts would continue and as a result, the weaker lines are intensified and the charge intensity differences between the various parts of the layer charge and, thus the diffracted beam, would be reduced giving an inaccurate reading. Thus, with the present invention, an accurate diffraction pattern is obtained since it is now possible for the weaker diffraction lines to be brought out sufficiently. In this way, while those portions of the charge pattern that are discharged to the maximum capacity level of the storage layer 30 (i.e., zero volts) will correspond to the diffraction peaks, the other portions of the charge pattern that are discharged to lower levels can be maximized without sacrificing the relative intensities of the diffracted beam, in contrast to some prior art techniques in which the intensity of the information corresponding to the diffraction peaks is not maximized and other portions of the charge pattern (and, thus, of the total information) is lost because the discharge at the weaker diffraction lines is insufficiently intensified to provide a measurable read-out. Thus, the present invention provides the capability of obtaining substantially all the information of the diffracted beam regardless of the relative intensities of the various beam parts. It may, however, be necessary to use a storage layer of high charge storage capacity in order to achieve the greatest degree of information.

It is further preferred that the present diffractometer device comprise a motor 50 that drives the rotatable member 34 by, e.g., by mounting the rotatable member 34 on the shaft 52 of the motor 50, by a drive belt, or by other means, a D.C. source 54 for providing electrical power to the corona discharge device 40, and a computer 56 to which information is transmitted by the sensors 42, 44. The computer 56 can receive the information from the following probe or sensor 44 to determine when the greatest discharge (i.e., saturation discharge, where the charge at the storage layer portion corresponding to the peak intensity at the diffracted x-ray beam) has been attained, the purpose thereof being, as above mentioned, to terminate the discharge of the storage layer or to read-out at that time the information in the storage layer, so as to maximize the intensity of the diffracted beam portions that are less than the diffraction peaks and, yet, maintain the relative intensities of the beam portions.

The probes or sensors 42, 44 preferably feed their information to corresponding amplifiers 58, 60 that each have an analog output and that each feed corresponding analog-to-digital converters 62, 64, which in turn, feed their respective information to the computer 56. The computer can be an FDC 302 controller or other suitable apparatus and can transmit the processed information from the reading sensor 42 to a printer 64 and feed back the information from the sensor 44 (the latter determining when maximum discharge of the storage layer has occurred.

An especially preferred mode of operation the present invention comprises reading out, via the reading sensor 42, the information embodied in the storage layer charge pattern, when the maximum discharge thereon (i.e., when the voltage level is zero or substantially zero) has been achieved, which would occur at the storage layer portions corresponding to the diffraction peak and storing this information. Thereafter, instead of recharging or refreshing the charge on the storage layer, the discharge of the storage layer is continued by continuing expose to the diffracted x-ray beam, that other portions of the storage layer (aside from those corresponding to the diffraction peaks, are further discharged to voltage levels of zero or approaching zero, the charge pattern being read-out intermittently and the read information being stored to obtain a cumulative read-out of the information. By this mode, the weaker diffraction lines are intensified to an even greater extent, but, yet, by continuously reading the charge pattern, the relative proportions of the various diffraction lines are maintained.

Thus, the present invention provides significant advantages including the practically simultaneous storing and reading of all the diffraction information, non-destructive sequential read-out during the process of recording information, feedback to control the information obtaining operation, and, importantly, the propagation and intensification of the weaker diffraction lines with the maintenance of the relative intensities of the various diffraction lines.

In another embodiment, the invention comprises an electrophotographic diffractometer apparatus 70 (FIG. 3) that comprises a substantially flat storage layer 72; a motor 74 and x-ray beam source (not shown) disposed at one side of the storage layer 72; a specimen boule 76 that is located on the other side of the storage layer 72 and optionally is mounted on an arc goniometer 78 that can be used to rotate the specimen 76; and a rotatable sensing head 80 that is capable of sweeping over the storage layer 72. As previously described, the sensing head 80 (FIG. 4) includes the elements (e.g., a rotating corona discharge device 82) that can provide on the storage layer a substantially uniform electrical charge and elements 84, 86 for measuring the charge on the storage layer 72 (e.g., two surface charge sensors or electron probes, with the corona discharge device 82 located therebetween).

The sensing head 80 can be located on an arm 88, with an aperture or passageway 90 extending through the pivot point, or shaft, about which the arm 88 rotates. The x-ray source is aligned with the passageway to permit a collimated primary x-ray beam 92 to pass therethrough and to strike the specimen 76, as a result of which the beam 92 is diffracted and back-scattered according to the characteristics of the specimen. The back-scattered beam 94 selectively discharges the storage layer 72, thereby providing a pattern of charges that comprise the information about the specimen 76, which information (i.e., the charge pattern) is read out by the sensing head 80, which is rotated by the motor 74. The read information can be processed with the system shown in FIG. 1.

In the sensing head 80, (FIG. 4) the leading probe 84 (e.g., an electrometer probe) can, as described above, measure the residual surface charge $E_{2\theta}$, while the following electrometer probe 86 measures the maximum surface charge $E_0$, with these values being treated as described above.

The specimen should be located on the central axis of the storage layer 72 so as to be in the path of the x-ray beam and to be on an axis substantially perpendicular to the plane of the storage layer to minimize image distortion arising from unequal distances of various corresponding parts of the storage layer from the specimen.

It can, therefore, be seen that the present invention provides not only the aforementioned advantages of maximizing the diffraction intensity peaks and yet maintaining the proportionate relationships between these peaks and the less intense diffraction lines, and other advantages, but also provides a dynamic system for diffraction work, compared with the static technique previously used.

What is claimed is:

1. An electrophotographic diffractometer apparatus comprising
   a. a photoconductive storage member;
   b. means for uniformly charging said storage member;
   c. means for holding a diffraction specimen;
   d. means for directing a collimated beam of electromagnetic radiation to said specimen, whereby diffracted rays of said beam are directed to said charge storage member and produce discharged local areas thereon in accordance with the diffraction characteristics of said specimen; and
   e. scanning means for electrically measuring the charge pattern at said storage member, said scanning means comprising said charging means and said measuring means.

2. An electrophotographic diffractometer apparatus as in claim 1, wherein said measuring means comprises a scanning device.

3. An electrophotographic diffractometer apparatus as in claim 1, wherein said scanning means is rotatable about said specimen holding means.

4. An electrophotographic diffractometer apparatus as in claim 1, wherein said measuring means comprising at least one electrostatic voltmeter.

5. An electrophotographic diffractometer apparatus as in claim 1, wherein said charging means comprises a corona discharge device.

6. An electrophotographic diffractometer apparatus as in claim 1, wherein said scanning means comprises means for providing an analog signal read-out of said charge pattern.

7. An electrophotographic diffraction apparatus as in claim 6, further comprising means for converting said analog signal to digital data and information processing means.

8. An electrophotographic diffractometer apparatus as in claim 7, further comprising automatic information feedback means to said sensing means.

9. An electrophotographic diffractometer apparatus as in claim 1, wherein said apparatus comprises a side wall defining a space, said specimen being disposed in said space, and said storage member comprises a layer disposed at the interior face of said side wall and substantially surrounding said specimen.

10. An electrophotographic diffractometer apparatus as in claim 1, comprising means for rotating said specimen while it is exposed to said radiation beam.

11. An electrophotographic diffractometer apparatus as in claim 1, wherein said storage member is substantially flat.

12. An electrophotographic diffractometer apparatus as in claim 11, wherein said specimen is disposed at one side of and on an axis perpendicular to said storage member.

13. An electrophotographic diffractometer apparatus as in claim 12, wherein said radiation a collimated x-ray beam and said apparatus comprises a source of said x-ray beam disposed at the other side of said storage member, said storage member comprising a passageway through which said x-ray beam is directed toward said specimen.

* * * * *

UNITED STATES PATENT AND TRADEMARK OFFICE
CERTIFICATE OF CORRECTION

PATENT NO. : 4,019,052
DATED : April 19, 1977
INVENTOR(S) : DAVID J. HAAS

It is certified that error appears in the above-identified patent and that said Letters Patent are hereby corrected as shown below:

In the Title, Section [73], "U.S. Philips Corporation"

should be --North American Philips Corporation--.

Signed and Sealed this second Day of August 1977

[SEAL]

Attest:

RUTH C. MASON
*Attesting Officer*

C. MARSHALL DANN
*Commissioner of Patents and Trademarks*